(12) United States Patent
Xu

(10) Patent No.: US 9,304,041 B2
(45) Date of Patent: Apr. 5, 2016

(54) ATOMIC ABSORPTION SPECTROMETER

(71) Applicant: SHENYANG HUAGUANG PRECISION INSTRUMENT CO., LTD., Shenyang (CN)

(72) Inventor: Peishi Xu, Shenyang (CN)

(73) Assignee: Shenyang Huaguang Precision Instrument Co., Ltd., Shenyang (CN)

( * ) Notice: Subject to any disclaimer, the term of this patent is extended or adjusted under 35 U.S.C. 154(b) by 225 days.

(21) Appl. No.: 13/940,234

(22) Filed: Jul. 11, 2013

(65) Prior Publication Data

US 2013/0301045 A1   Nov. 14, 2013

Related U.S. Application Data

(63) Continuation-in-part of application No. PCT/CN2011/077860, filed on Aug. 1, 2011.

(51) Int. Cl.
| | |
|---|---|
| *G01J 3/30* | (2006.01) |
| *G01J 3/42* | (2006.01) |
| *G01N 21/31* | (2006.01) |
| *G01N 21/72* | (2006.01) |

(52) U.S. Cl.
CPC .............. *G01J 3/42* (2013.01); *G01N 21/3103* (2013.01); *G01N 21/72* (2013.01)

(58) Field of Classification Search
CPC ............. G01N 21/71–21/74; G01N 2021/712; G01N 2021/725; G01N 2021/745; G01N 21/3103; G01J 3/42
See application file for complete search history.

(56) References Cited

FOREIGN PATENT DOCUMENTS

| CN | 2909245 Y | * | 6/2007 |
|---|---|---|---|
| CN | 101097186 A | * | 1/2008 |

OTHER PUBLICATIONS

Google Translation of CN 2909245 Y.*
Espacenet Abstract Translation of CN 101097186 A.*

* cited by examiner

*Primary Examiner* — Michael A Lyons
*Assistant Examiner* — Shawn Decenzo
(74) *Attorney, Agent, or Firm* — Novick, Kim & Lee, PLLC; Allen Xue

(57) ABSTRACT

An atomic absorption spectrometer, including: a light source combination; a detection device; a flame atomization device; a hydride generation device; a graphite furnace atomization device; and an adjustment mechanism. The flame atomization device includes a flame atomizer. The hydride generation device includes a hydride atomizer. The graphite furnace atomization device includes a graphite furnace atomizer. An axis of the flame atomizer, an axis of the hydride atomizer, and an axis of the graphite furnace atomizer are adjusted by the adjustment mechanism to coincide with an optical axis of the light source combination.

9 Claims, 7 Drawing Sheets

ATOMIC ABSORPTION SPECTROMETER

CROSS-REFERENCE TO RELATED APPLICATIONS

This application is a continuation-in-part of International Patent Application No. PCT/CN2011/077860 with an international filing date of Aug. 1, 2011, designating the United States, now pending, and further claims priority benefits to Chinese Patent Application No. 201110005907.3 filed Jan. 12, 2011. The contents of all of the aforementioned applications, including any intervening amendments thereto, are incorporated herein by reference. Inquiries from the public to applicants or assignees concerning this document or the related applications should be directed to: Matthias Scholl P. C., Attn.: Dr. Matthias Scholl Esq., 14781 Memorial Drive, Suite 1319, Houston, Tex. 77079.

BACKGROUND OF THE INVENTION

1. Field of the Invention

The invention relates to an elemental analyzer, and more particularly to an atomic absorption spectrometer.

2. Description of the Related Art

Atomic absorption spectrometer employs a flame atomization method to measure a plurality of metal elements of micro content (ug/l), and employs a graphite furnace atomization method to measure elements of trace content (ng/l). However, some elements cannot be measured by the flame atomization method or the graphite furnace atomization method, such as Hg and a trace content of As and Se. Thus, a hydride generation device is required by the atomic absorption spectrometer. A typical atomic absorption spectrometer either has a single function or is integrated with the graphite furnace atomization device. For trace measurement of Hg, As, and Se, which cannot be realized by the two methods, the hydride generation device and the hydride atomizer are required. In use, the two devices are switched and adjusted manually, the control of which is inconvenient and time consuming. The devices have large volumes thereby occupying large space in the lab. Furthermore, the hydride generation device has a complicate structure and is provided with a plurality of pipelines and interfaces, thus, the failure rate of the hydride generation device is high. During the switching of the atomization methods, the hydride atomizer is easy to damage, thereby increasing the facility cost and affecting the working efficiency.

SUMMARY OF THE INVENTION

In view of the above-described problems, it is one objective of the invention to provide an atomic absorption spectrometer that is able to realize automatically switching control of a plurality of atomization devices and pipelines integration of the hydride generation device.

To achieve the above objective, in accordance with one embodiment of the invention, there is provided an atomic absorption spectrometer. The atomic absorption spectrometer comprises: a light source combination; a detection device; a flame atomization device, the flame atomization device comprising a flame atomizer; a hydride generation device, the hydride generation device comprising a hydride atomizer; a graphite furnace atomization device, the graphite furnace atomization device comprising a graphite furnace atomizer; and an adjustment mechanism. An axis of the flame atomizer, an axis of the hydride atomizer, and an axis of the graphite furnace atomizer are adjusted by the adjustment mechanism to coincide with an optical axis of the light source combination.

In a class of this embodiment, the adjustment mechanism comprises: a first adjustment mechanism for adjusting positions of the flame atomizer and the hydride atomizer; and a second adjustment mechanism for adjusting a position of the graphite furnace atomizer. The first adjustment mechanism and the second adjustment mechanism are independently arranged. The first adjustment mechanism comprises: a horizontal adjustment device, and a vertical adjustment device. The vertical adjustment device is disposed on the horizontal adjustment device and is capable of moving horizontally. The flame atomizer and the hydride atomizer are in rigid connection and are arranged horizontally in parallel above the vertical adjustment device.

In a class of this embodiment, the second adjustment mechanism is horizontally movable through a transmission mechanism of a third lead screw. The graphite furnace atomizer is disposed on the second adjustment mechanism. A height of the axis of the graphite furnace atomizer is equal to a height of the optical axis.

In a class of this embodiment, a division plate is disposed between the first adjustment mechanism and the second adjustment mechanism. The first adjustment mechanism and the optical axis of the light source combination are disposed on one side of the division plate. The second adjustment mechanism is disposed on the other side of the division plate. The division plate comprises an opening for allowing the graphite furnace atomizer to pass through.

In a class of this embodiment, the hydride generation device comprises at least two base plates matching with each other to form a seal structure. The base plates are provided with grooves. The grooves comprise a plurality of functional zones which are connected to form an integrated hydride generation device.

In a class of this embodiment, the functional zones comprise zones for accommodating a dispenser, a reactor, a carrier pump, a sample pump, a reductant pump, and an auxiliary gas pump, respectively. The dispenser and the reactor are disposed on a first base plate in the form of the grooves. The first base plate is further provided with a sample inlet, a reductant inlet, a carrier inlet, a working gas interface, and a pinch valve interface. The carrier pump, the sample pump, the reluctant pump, and the auxiliary gas pump are disposed on a second base plate in the form of the grooves. The second base plate is further provided with a gas-liquid separator, an effluent outlet, and a hydride outlet. The first base plate is clasped on the second base plate. The grooves arranged on the base plates communicate through corresponding vias. The first base plate is provided with a sealing cover.

In a class of this embodiment, a first, second, and third buffer pools are provided and arranged at inlets of the carrier pump, the sample pump, and the reductant pump, respectively.

In a class of this embodiment, the carrier pump, the sample pump, the reductant pump, and the auxiliary gas pump have the same structures and employ a self-priming pump.

In a class of this embodiment, a first valve is arranged on a by-path of a sample inlet of the sample pump for purging a sample inlet pipe.

In a class of this embodiment, a second valve is disposed between the dispenser and the effluent outlet for preventing disturbance caused by a sample residue from a prior test.

In a class of this embodiment, the carrier pump, the reductant pump, and the auxiliary gas pump have the same structures and employ a self-priming pump. The sample pump is a syringe pump.

Advantages of the invention are summarized as follows:

1. The atomic absorption spectrometer of the invention is integrated with three atomizers for achieving fast, direct, and effective measurement of microelements and trace elements, such as Hg, As, and Se. The detection process by the atomic absorption spectrometer of the invention is simple and convenient.

2. The invention achieves automatically switching control and pipelines integration. The atomic absorption spectrometer is integrated with the graphite furnace atomization device and the hydride generation device, thereby being convenient to operate. The original flame atomizer of the atomic absorption spectrometer, the graphite furnace atomization device, and the hydride generation device can be switched automatically, the process of which is simple, and does not damage the atomizers. The integrated hydride generation device has more stable function and reliable quality.

BRIEF DESCRIPTION OF THE DRAWINGS

The invention is described hereinbelow with reference to the accompanying drawings, in which.

DETAILED DESCRIPTION OF THE EMBODIMENTS

For further illustrating the invention, experiments detailing an atomic absorption spectrometer are described below. It should be noted that the following examples are intended to describe and not to limit the invention.

EXAMPLE 1

Figure 1:
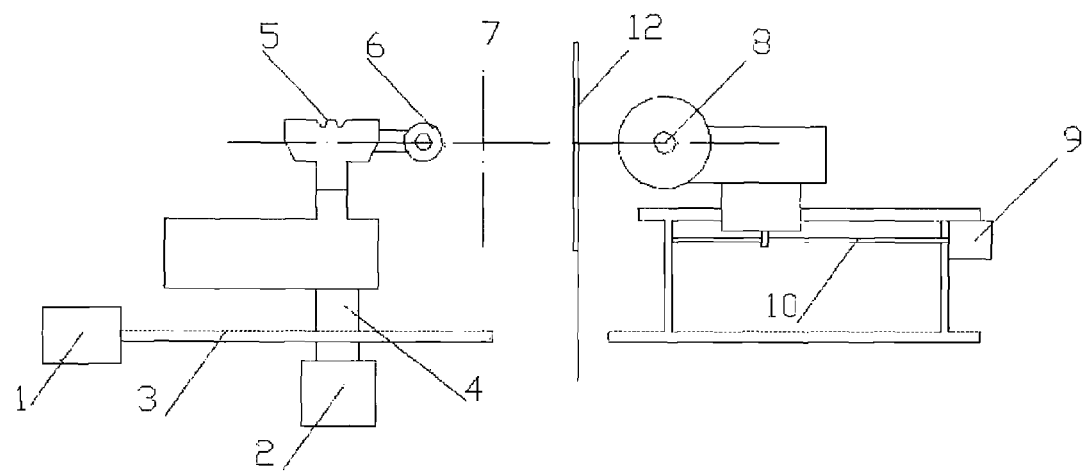
FIG. 1 is a structure diagram of atomization devices of an atomic absorption spectrometer in accordance with one embodiment of the invention.

As shown in FIG. 1, an atomic absorption spectrometer comprises: a light source combination; a detection device; a flame atomization device, the flame atomization device comprising a flame atomizer 5; a hydride generation device, the hydride generation device comprising a hydride atomizer 6; a graphite furnace atomization device, the graphite furnace atomization device comprising a graphite furnace atomizer 8; and an adjustment mechanism. An axis of the flame atomizer 5, an axis of the hydride atomizer 6, and an axis of the graphite furnace atomizer 8 are adjusted by the adjustment mechanism to coincide with an optical axis 7 of the light source combination.

The adjustment mechanism comprises: a first adjustment mechanism for adjusting positions of the flame atomizer 5 and the hydride atomizer 6; and a second adjustment mechanism for adjusting the position of the graphite furnace atomizer 8. The first adjustment mechanism and the second adjustment mechanism are independently arranged. The first adjustment mechanism comprises: a horizontal adjustment device, and a vertical adjustment device. The vertical adjustment device is disposed on the horizontal adjustment device and is capable of moving horizontally. The flame atomizer 5 and the hydride atomizer 6 are in rigid connection and are arranged horizontally in parallel above the vertical adjustment device. The vertical adjustment device is vertically movable driven by a first lead screw 4 of a first motor 2; and the horizontal adjustment device is horizontally movable driven by a second lead screw 3 of a second motor 1. The second adjustment mechanism is horizontally movable driven by a third lead screw 10 of a third motor 9. The graphite furnace atomizer 8 is disposed on the second adjustment mechanism. A height of the axis of the graphite furnace atomizer 8 is equal to a height of the optical axis 7. A division plate 12 is disposed between the first adjustment mechanism and the second adjustment mechanism. The first adjustment mechanism and the optical axis 7 of the light source combination are disposed on one side of the division plate 12. The second adjustment mechanism is disposed on the other side of the division plate 12. The division plate 12 comprises an opening for allowing the graphite furnace atomizer 8 to pass through. The opening is provided with a door on which a carriage is arranged, and the graphite furnace atomizer 8 is provided with a guide wheel so as to form a rolling contact between the guide wheel and the carriage.

The hydride generation device comprises at least two base plates matching with each other to form a seal structure. The base plates are provided with grooves. The grooves comprise a plurality of functional zones which are connected to form an integrated hydride generation device.

Figure 2:
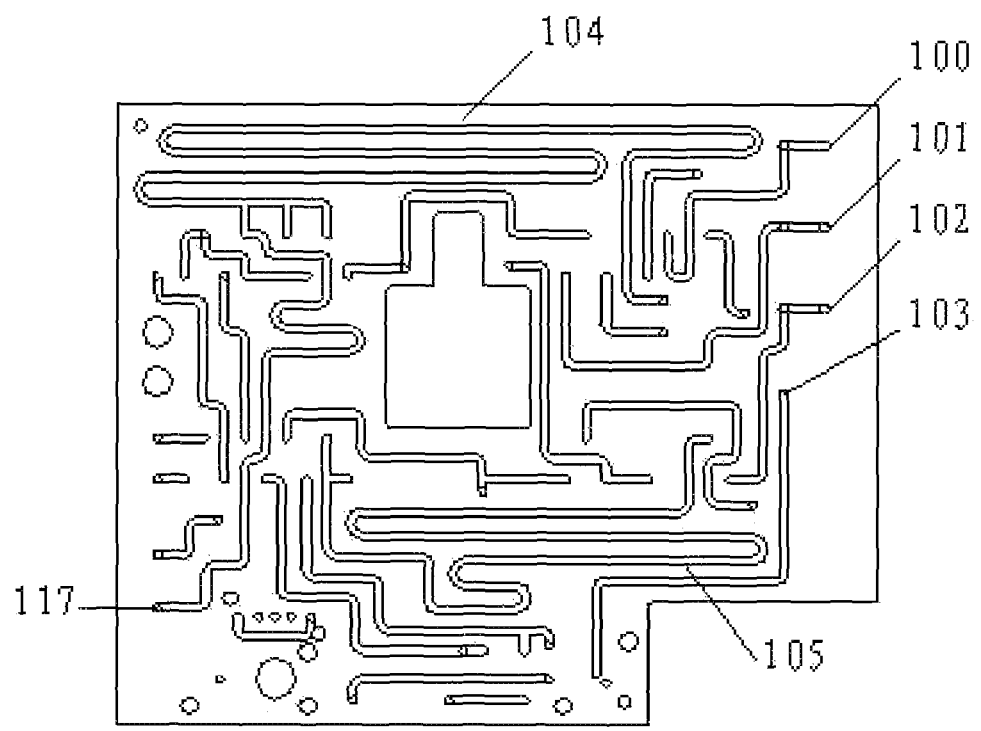
FIG. 2 is a structure diagram of a first base plate of a hydride generation device in accordance with a first embodiment of the invention.
Figure 3:
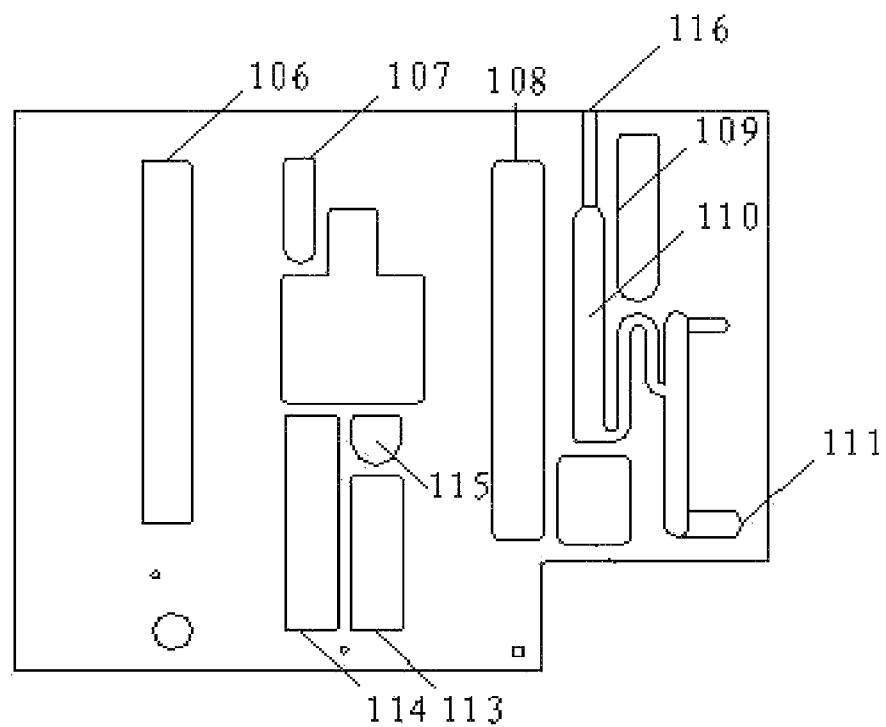
FIG. 3 is a structure diagram of a second base plate of a hydride generation device in accordance with a first embodiment of the invention.

As shown in FIGS. 2-3, the functional zone comprises zones for accommodating a dispenser 105, a reactor 104, a carrier pump 108, a sample pump 114, a reductant pump 113, and an auxiliary gas pump 106, respectively. The dispenser 105 and the reactor 104 are disposed on a first base plate in the form of the grooves. The first base plate is further provided with a sample inlet 100, a reductant inlet 101, a carrier inlet 102, an auxiliary gas inlet 103, a working gas interface 117, and a pinch valve interface. The carrier pump 108, the sample pump 114, the reluctant pump 113, and the auxiliary gas pump 106 are disposed on a second base plate in the form of the grooves. The second base plate is further provided with a gas-liquid separator 110, an effluent outlet 111, and a hydride outlet 116. The first base plate is clasped on the second base plate. The grooves arranged on the base plates communicate through corresponding vias. The first base plate is provided with a sealing cover. A first, second, and third buffer pools 107, 109, and 115 are provided and arranged at inlets of the carrier pump 114, the sample pump 108, and the reductant pump 113, respectively.

The base plates are made from polymethylmethacrylate, which are processed into functional zones for accommodating pipes, the dispenser 105 and the reactor 104, and into functional zones (pump zones) for accommodating the sample pump 114, the reductant pump 113, and the auxiliary gas pump 106. The pipes have a width of 1 mm and a depth of 1.5 mm after being processed by a spherical cutter having a radius of 1 mm. A lower part of a cross section of the processed pipe is semicircle-shaped so as to facilitate the flow of the solution. The pump zones have a width of 11 mm, and a depth of 11 mm. The length of the pumps is determined according to practical requirements. A first, second, and third buffer pools 107, 109, and 115 are provided and arranged on the inlets of the pumps for preventing the reagents from contacting with the pumps, respectively. After functional parts are assembled, stick the first base plate and the second base plate together, and use another polymer plate to stick to the first base plate for sealing. Connect different plates by circular vias, mount interfaces and valves, and finally connect to a control circuit. Thus, the hydride generation device having a compact structure and small volume is produced.

Working process of the hydride generation device is as follows:

Introduce reagents from the sample inlet 100, the reductant inlet 101, and the carrier inlet 102 to corresponding buffer pools, respectively, under the force of pumps. Carry out reaction in the reactor 104, and separate a produced gas from effluent by the gas-liquid separator 110. Introduce a separated gas to the hydride atomizer for measurement, and discharge the effluent from the effluent outlet. The whole structure is formed by machining, thereby ensuring a consistent and simplified structure, largely decreasing the number of pipelines interfaces, and eliminating fault points.

EXAMPLE 2

Figure 4:
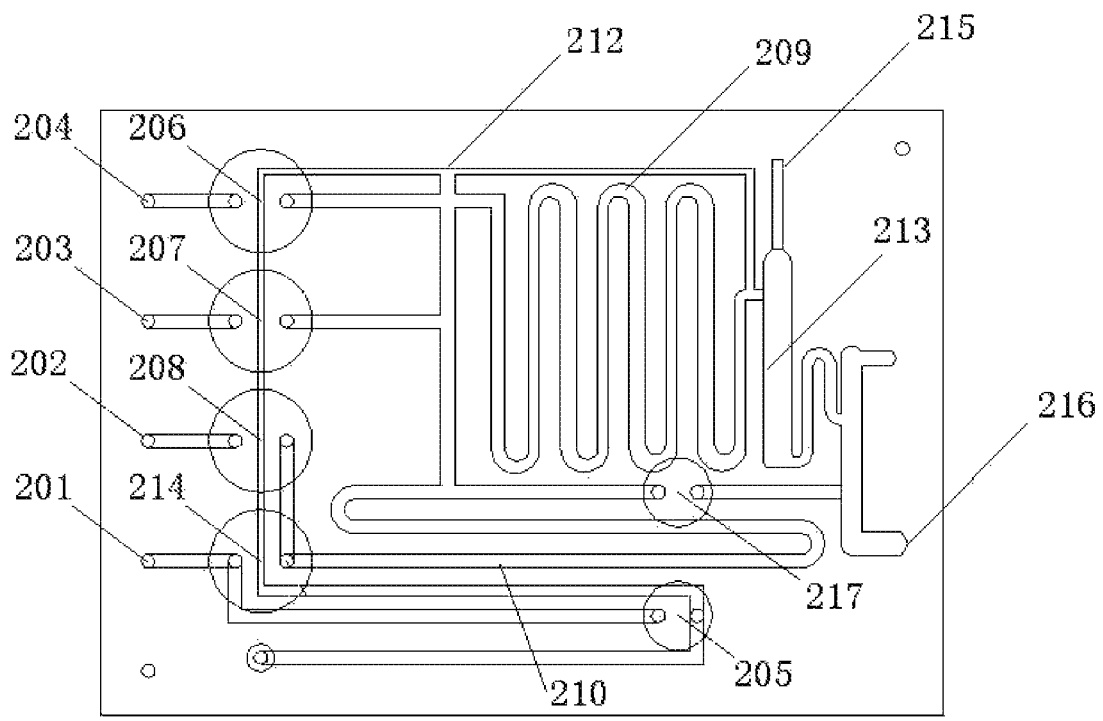
FIG. 4 is a structure diagram of a base plate of a hydride generation device in accordance with a second embodiment of the invention.
Figure 5:
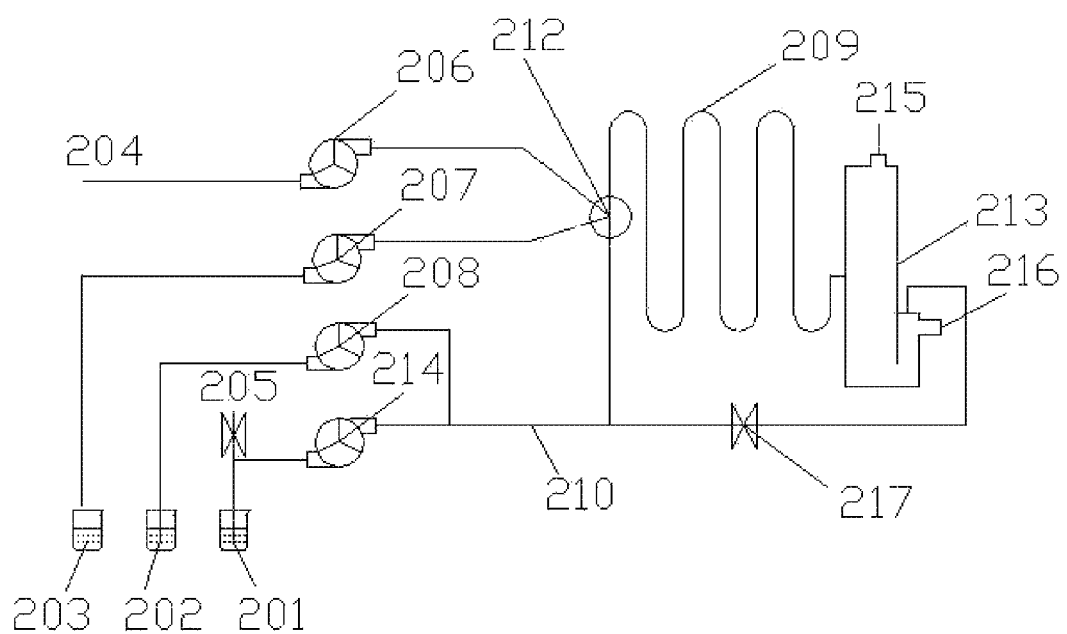
FIG. 5 is a schematic diagram of a hydride generation device in accordance with a second embodiment of the invention.

As shown in FIGS. 4-5, the atomic absorption spectrometer is the same as that in Example 1 except that: the carrier pump 208, the sample pump 214, the reductant pump 207, and an auxiliary gas pump 206 have the same structure and employ a self-priming pump. A second valve 217 is disposed between the dispenser 210 and the effluent outlet 216.

To collect the sample, open the second valve 217 and close the first valve 205 so as to suck the sample under the force of the sample pump 214 and dispense the sample by the dispenser 210. The sample cannot be lifted to the interface but can only be introduced out from the opened second valve 217. Thus, while dispensing the sample by the dispenser 210, a sample residue from a prior test is removed. After the sample is collected, stop the sample pump 214, close the second valve 217, and start other pumps. Suck the carrier 202 under the force of the carrier pump 208, and meanwhile the carrier 202 pushes the sample from the dispenser 210 to the interface 212 so as to allow the sample to be mixed and react with the reductant 203 and the auxiliary gas 204 in the interface 212. After a complete reaction of a mixed solution in a reaction tube 209, separate gas from effluent by a separator 213. Introduce the gas from a hydride outlet 215 to the hydride atomizer for measurement, and discharge the effluent from an effluent outlet 216. After collecting the sample, open the first valve 205 to introduce the air to remove the sample residue between the sample interface 201 and the sample pump 214 so as to prevent a posterior sample from being polluted. The speed of the self-priming pumps for sucking the sample is adjusted by a control circuit according to different samples to be measured, thereby improving the performance of the measurement.

EXAMPLE 3

Figure 6:
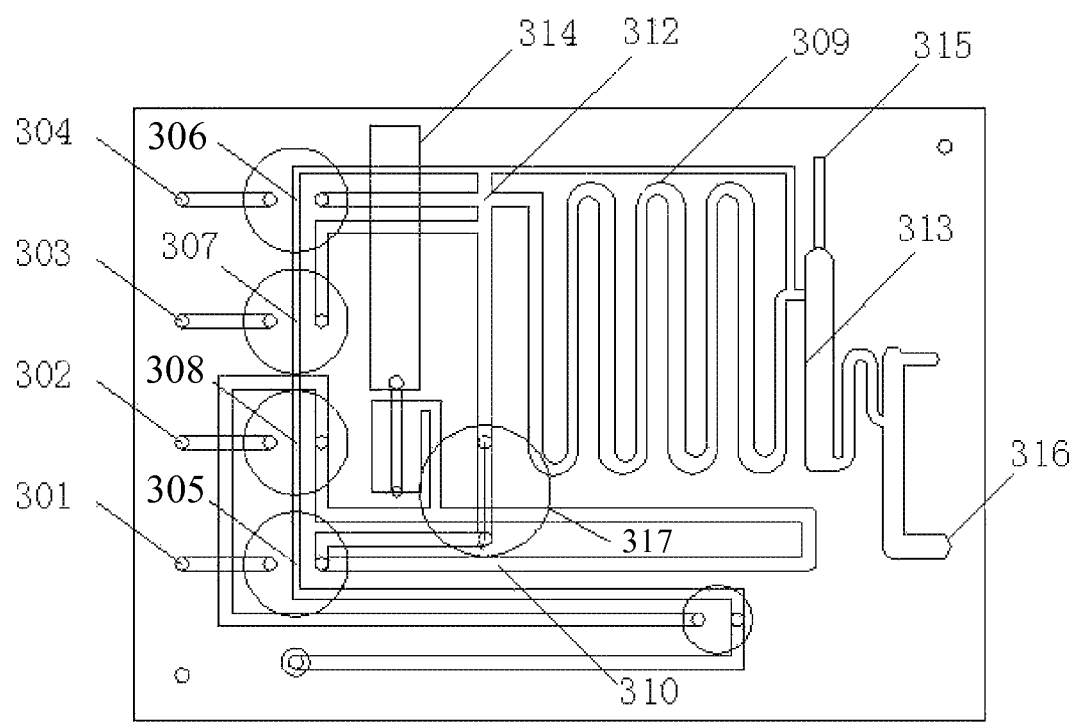
FIG. 6 is a structure diagram of a base plate of a hydride generation device in accordance with a third embodiment of the invention.
Figure 7:
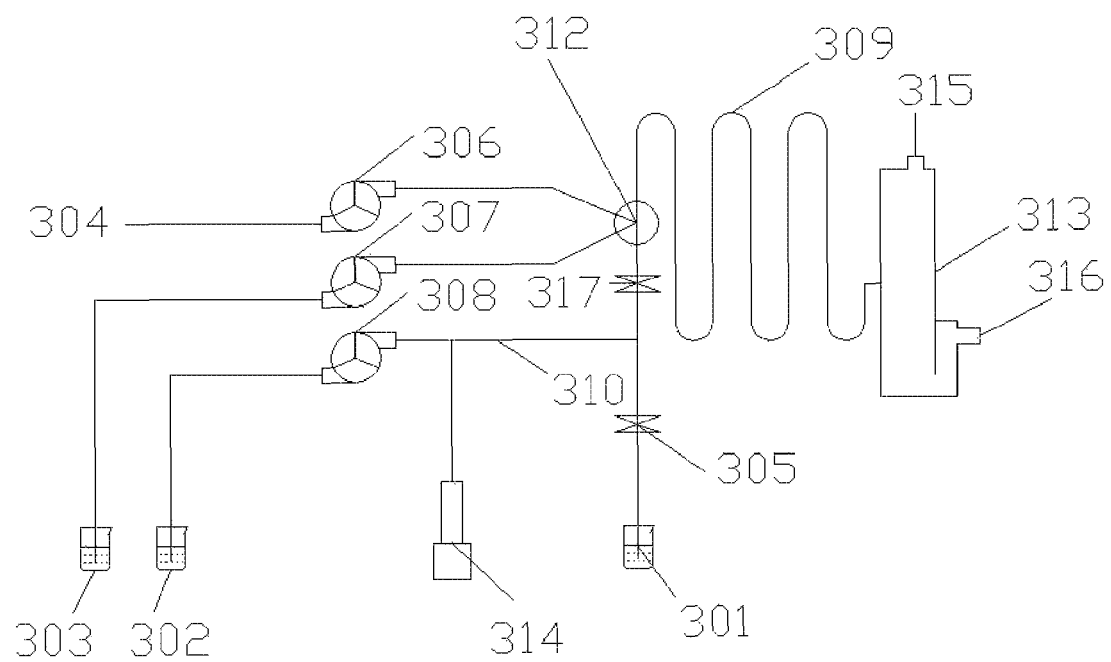
FIG. 7 is a schematic diagram of a hydride generation device in accordance with a third embodiment of the invention.

As shown in FIGS. 6-7, the reference numbers 301, 302, 303, and 304 correspond to the reference numbers 201, 202, 203, and 204 in Example 2. The carrier pump 308, the reductant pump 307, and the auxiliary gas pump 306 have the same structures and employ a self-priming pump. The sample pump 314 is a syringe pump. A first valve 305 is arranged on a by-path of a sample inlet of the sample pump for purging a sample inlet pipe.

The sample is suck by the syringe pump. Open the first valve 305 and close the second valve 317 for allowing the sample pump 314 to suck the sample and the dispenser 310 to dispense the sample. After that, close the first valve 305 and open the second valve 317 so as to suck the carrier and push the sample from the second valve 317 to the interface 312. Mix the sample with the reductant and the air to carry out reaction in a reaction tube 309. Introduce a resulting solution in a gas-liquid separator 313 to separate gas from effluent. Introduce the gas from the hydride outlet 315 to the hydride atomizer for measurement, and discharge the effluent from an effluent outlet 316.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:

1. An atomic absorption spectrometer, comprising:
   a flame atomization device, the flame atomization device comprising a flame atomizer;
   a hydride generation device, the hydride generation device comprising a hydride atomizer;
   a graphite furnace atomization device, the graphite furnace atomization device comprising a graphite furnace atomizer; and
   an adjustment mechanism,
   wherein an axis of the flame atomizer, an axis of the hydride atomizer, and an axis of the graphite furnace atomizer are adjusted by the adjustment mechanism to coincide with an optical axis of a light source and detector combination,
   wherein the hydride generation device comprises at least two base plates matching with each other to form a seal structure; the base plates are provided with grooves; and the grooves comprise a plurality of functional zones which are connected to form an integrated hydride generation device,
   wherein the functional zones comprise zones for accommodating a dispenser, a reactor, a carrier pump, a sample pump, a reductant pump, and an auxiliary gas pump, respectively; the dispenser and the reactor are disposed on a first base plate in the form of the grooves; the first base plate is further provided with a sample inlet, a reductant inlet, a carrier inlet, a working gas interface, and a pinch valve interface; the carrier pump, the sample pump, the reductant pump, and the auxiliary gas pump are disposed on a second base plate in the form of the grooves; the second base plate is further provided with a gas-liquid separator, an effluent outlet, and a hydride outlet; the first base plate is clasped on the second base plate; the grooves arranged on the base plates communicate through corresponding vias; and the first base plate is provided with a sealing cover.

2. The atomic absorption spectrometer of claim 1, wherein the adjustment mechanism comprises: a first adjustment mechanism for adjusting positions of the flame atomizer and the hydride atomizer; and a second adjustment mechanism for adjusting a position of the graphite furnace atomizer;
   the first adjustment mechanism and the second adjustment mechanism are independently arranged;

the first adjustment mechanism comprises: a horizontal adjustment device, and a vertical adjustment device;

the vertical adjustment device is disposed on the horizontal adjustment device and is capable of moving horizontally; and the flame atomizer and the hydride atomizer are in rigid connection and are arranged horizontally in parallel above the vertical adjustment device.

3. The atomic absorption spectrometer of claim 2, wherein the second adjustment mechanism is horizontally movable through a transmission mechanism of a third lead screw;

the graphite furnace atomizer is disposed on the second adjustment mechanism; and a height of the axis of the graphite furnace atomizer is equal to a height of the optical axis.

4. The atomic absorption spectrometer of claim 2, wherein a division plate is disposed between the first adjustment mechanism and the second adjustment mechanism;

the first adjustment mechanism and the optical axis of the light source combination are disposed on one side of the division plate;

the second adjustment mechanism is disposed on the other side of the division plate; and the division plate comprises an opening for allowing the graphite furnace atomizer to pass through.

5. The atomic absorption spectrometer of claim 1, wherein a first buffer pool, a second buffer pool, and a third buffer pool are provided and arranged at inlets of the carrier pump, the sample pump, and the reductant pump, respectively.

6. The atomic absorption spectrometer of claim 1, wherein the carrier pump, the sample pump, the reductant pump, and the auxiliary gas pump have a same structure and employ a self-priming pump.

7. The atomic absorption spectrometer of claim 1, wherein a first valve is arranged on a by-path of the sample inlet of the sample pump for purging a sample inlet pipe.

8. The atomic absorption spectrometer of claim 1, wherein a second valve is disposed between the dispenser and the effluent outlet for preventing disturbance caused by a sample residue from a prior test.

9. The atomic absorption spectrometer of claim 1, wherein the carrier pump, the reductant pump, and the auxiliary gas pump have the same structures and employ a self-priming pump; and the sample pump is a syringe pump.

* * * * *